(12) United States Patent
Terwilliger et al.

(10) Patent No.: US 6,786,858 B2
(45) Date of Patent: Sep. 7, 2004

(54) DELIVERY SYSTEM AND METHOD FOR INTERSTITIAL RADIOTHERAPY USING HOLLOW SEEDS

(75) Inventors: Richard A. Terwilliger, Southbury, CT (US); Gary A. Lamoureux, Woodbury, CT (US)

(73) Assignee: IdeaMatrix, Inc., Estes Park, CO (US); part interest ( * ) Notice: Subject to any disclaimer, the term of this patent is extended or adjusted under 35 U.S.C. 154(b) by 0 days.

(21) Appl. No.: 10/132,930

(22) Filed: Apr. 26, 2002

(65) Prior Publication Data

US 2003/0088144 A1 May 8, 2003

Related U.S. Application Data

(60) Provisional application No. 60/336,329, filed on Nov. 2, 2001, and provisional application No. 60/360,260, filed on Feb. 26, 2002.

(51) Int. Cl.$^7$ .............................................. A61N 5/00
(52) U.S. Cl. ........................................................ 600/3
(58) Field of Search .............................. 600/1–8, 433, 600/585; 428/68, 138, 2, 112, 218, 34.9, 35.1; 264/342 R; 403/404, 267; 24/67 CF; 411/183, 258, 501, 546, 82; 378/20

(56) References Cited

U.S. PATENT DOCUMENTS

| | | | |
|---|---|---|---|
| 1,578,945 A | 3/1926 | Withers | |
| 2,067,589 A | 1/1937 | Antrim | |
| 3,351,049 A | 11/1967 | Lawrence | |
| 3,565,869 A | 2/1971 | Prospero | 260/78.3 |
| 3,636,956 A | 1/1972 | Schneider | |
| 4,052,988 A | 10/1977 | Doddi et al. | |
| 4,086,914 A | 5/1978 | Moore | |
| 4,167,179 A | 9/1979 | Kirsch | |
| 4,402,308 A | 9/1983 | Scott | |
| 4,509,506 A | 4/1985 | Windorski et al. | |
| 4,697,575 A | 10/1987 | Horowitz | |
| 5,339,812 A | 8/1994 | Hardy et al. | 128/653.1 |
| 5,460,592 A * | 10/1995 | Langton et al. | 600/7 |
| 5,713,828 A * | 2/1998 | Coniglione | 600/7 |
| 5,761,877 A | 6/1998 | Quandt | 63/155 |
| 5,833,593 A * | 11/1998 | Liprie | 600/3 |
| 6,039,684 A * | 3/2000 | Ildstad et al. | 600/1 |
| 6,080,099 A * | 6/2000 | Slater et al. | 600/8 |
| 6,132,677 A | 10/2000 | Ohriner | |
| 6,132,947 A | 10/2000 | Honan et al. | |
| 6,159,143 A * | 12/2000 | Lennox | 60/4 |
| 6,200,256 B1 | 3/2001 | Weinberger | |
| 6,248,057 B1 * | 6/2001 | Mavity et al. | 600/3 |
| 6,283,911 B1 * | 9/2001 | Keren | 600/3 |
| 6,312,374 B1 * | 11/2001 | von Hoffmann | 600/3 |
| 6,398,709 B1 * | 6/2002 | Ehr et al. | 600/3 |
| 6,497,646 B1 * | 12/2002 | Candelaria et al. | 600/7 |
| 6,514,193 B2 * | 2/2003 | Kaplan | 600/7 |
| 6,537,193 B1 | 3/2003 | Lennox | |
| 6,539,247 B2 | 3/2003 | Spetz | 600/427 |

FOREIGN PATENT DOCUMENTS

EP      0 030 822      9/1983      ........... A61L/17/00

OTHER PUBLICATIONS

Middleton et al., "Synthetic Biodegradable Polymers as Medical Devices"; Medical Plastic and Biomaterials Magazine; MPB Article Index; Originally published Mar. 1998; 6 pages.
Brochure entitled: OncoSeed™ (Iodine–125–Seeds); Medical–Physics Inc., 43–6711C; Rev. Oct. 1999; 2 pages.
Brochure entitled: OscoSeed™ (Iodine–125–Seeds); "Rapid Strand" Rigid Absorbable Permanent Implant Device; Medical–Physics Inc., Revised Oct. 1999; 2 pages.
Amersham Health; "EchoSeed™"; htt://www.amersham-health–us.com/echoseed/printed Nov. 19, 2003.
Amersham Health; "Rapid Strand Indications" Http;//www.amershamhealth–us.com/products/index.htp?a=i&i=38; printed Nov. 19, 2003.
Amersham Health; OncoSeed™ (Iodine–125 Seeds) http://www.amershamhealty–us.com/oncoseed/; printed Nov. 19, 2003.

* cited by examiner

*Primary Examiner*—Eric F. Winakur
*Assistant Examiner*—Nikita R Veniaminov
(74) *Attorney, Agent, or Firm*—Fliesler Meyer LL

(57) ABSTRACT

A delivery system and method for interstitial radiation therapy uses a seed strand composed of a plurality of tubular shaped, hollow radioactive seeds with a bore. The seed strand as assembled with a material provided in the bore and between the spaced seeds is axially stiff and radially flexible and is bioabsorbable in living tissue.

73 Claims, 1 Drawing Sheet

DELIVERY SYSTEM AND METHOD FOR INTERSTITIAL RADIOTHERAPY USING HOLLOW SEEDS

CLAIM OF PRIORITY

This application claims priority from U.S. Provisional Patent No. 60/336,329 flied on Nov. 2, 2001, and this application claims priority from U.S. Provision Patent Application No. 60/360,260 filed on Feb. 26, 2002, which applications are incorporated herein by reference. This application claims priority from U.S. patent application Ser. No. 10/035,083 filed on Dec. 28, 2001, which is incorporated herein by reference.

CROSS REFERENCE TO RELATED APPLICATIONS

The following applications are cross-referenced and incorporated herein by reference:

U.S. Patent Application No. 60/360,241 entitled "Delivery System and Method for Interstitial Radiation Therapy Using Seed Strands Constructed With Preformed Strand Housing," by Terwilliger et al., filed Feb. 26, 2002. (WORLD1000US2)

U.S. Patent Application No. 60/360,237 entitled "System for Manufacturing Interstitial Radiation Therapy Seed Strands," by Terwilliger et al., filed Feb. 26, 2002. (WORLD-01000US3)

U.S. Patent Application No. 60/360,272 entitled "Delivery System and Method for Interstitial Radiation Therapy Using Strands Constructed With Extruded Strand Housing," by Terwilliger et al., filed Feb. 26, 2002. (WORLD-01000US4)

U.S. Patent Application No. 60/360,299 entitled "Delivery System and Method for Interstitial Radiation Therapy Using Seed Elements With Ends Having One of Projections and Indentations," by Terwilliger et al., filed Feb. 26, 2002. (WORLD-01003US0)

FIELD OF INVENTION

The present invention relates to systems and methods for delivering a plurality of radioactive sources to a treatment site.

BACKGROUND

In interstitial radiation therapy, one method for treating tumors is to permanently place small, radioactive seeds into the tumor site. This method is currently accomplished by one of the following two procedures: (a) loose seeds are implanted in the target tissue, and/or (b) seeds are contained within a woven or braided absorbable carrier such as braided suture material and implanted in the target tissue. The loose seeds, however, are dependent on the tissue itself to hold each individual seed in place during treatment, and the woven or braided sutures do not assist in the placement of the seeds relative to the target tissue.

There have been many developments in brachytherapy (i.e. therapy relating to treating malignant tumors, which use such radioactive seeds). In one technique, hollow metal needles are inserted into the tumor, and the seeds are thereafter inserted into the needles, while the needles are being retracted to deposit the seeds in the tumor. Such devices are shown in U.S. Pat. No. 4,402,308 which is incorporated herein by reference. The most commonly used instruments are the Henschke and Mick devices. The use of such devices has distinct disadvantages. The overall length of such devices is over 20 cm and such devices have significant weight making them difficult to manipulate.

Another disadvantage of the above technique is that the seeds are deposited in a track made by the needle. When the needle is withdrawn, there is a tendency for the seeds to migrate in that track resulting in a poor distribution of the seeds. Because the energy levels are low, distribution between centers of adjacent seeds should be on the order of about 1 cm for certain treatments. Poor distribution of seeds can result in undesirable concentrations of seeds resulting in either an over-dosage or under-dosage of radiation. Further, over time, the seeds tend to migrate along the needle track, away from the tumor, and accordingly patients commonly must repeat the procedure within a couple months to have seeds re-implanted near the tumor.

Further complicating the procedure is the fact that the seeds are small, because they need to fit in small bore needles to prevent excessive tissue damage. Due to their small size and high seed surface dose, the seeds are difficult to handle and to label, and can easily be lost. In addition, the technique of implantation of individual seeds is time consuming.

One preferred method of introducing seeds into the tumor site is using a pre-manufactured elongated assembly or implant that contains seeds spaced at 1 cm increments. This assembly is capable of being loaded into an introducer needle just prior to the procedure. What is desired in using an elongated assembly of seeds and spacers is the ability to insert such an assembly into a tumor site to provide controlled and precise placement of the radioactive seeds.

While assemblies with bio-absorbable materials and spaced radioactive seeds are known for use as interstitial implants, such assemblies are not entirely satisfactory. In one instance, the elongated implant is made using a bio-absorbable material consisting of an Ethicon Vicryl.RTM. This material is commonly known as PGA. Radioactive seeds and teflon spacers are inserted into the material. Needles loaded with the seeds in the carrier bio-absorbable material are sterilized or autoclaved causing contraction of the carrier material and resulting in a rigid column of seeds and spacers. This technique was reported in "Ultrasonically Guided Transperineal Seed Implantation of the Prostate: Modification of the Technique and Qualitative Assessment of Implants" by Van't Riet, et al., International Journal of Radiation Oncology, Biology and Physics, Vol. 24, No. 3, pp. 555–558, 1992 which is incorporated herein by reference. Such rigid implants have many drawbacks, including not having the ability to flex with the tissue over the time that the bio-absorbable material dissolves.

As the tissue or glands shrink back to pre-operative size, and thus as the tissue recedes, a rigid elongated implant does not move with the tissue, but remain stationary relative to the tissue or gland. The final location relative to the tumor is thus not maintained and the dosage of the radioactive seeds does not meet the preoperative therapy plan.

Another system for providing an elongated implant having radioactive seeds disposed therein is disclosed in U.S. Pat. No. 4,697,575 which is incorporated herein by reference. In this reference, a plurality of encapsulated radioactive seeds are positioned in a predetermined array. The seeds are encapsulated in individual capsules, with each capsule having a projection on one capsule end and a complementary recess on the remaining capsule end. A projection in one capsule is engageable with a recess in an adjacent capsule such that the desired number of seeds can be plugged together to form a column of rigid, bio-absorbable and elongated material. This implant is not entirely satisfactory inasmuch as it is time consuming and inefficient to carry out the manipulative steps of assembling such a strand of elongated material. Further the implant is quite rigid as it is inserted into a patient without the use of an introduction needle, as the implant itself acts as a rigid needle that is undesirably left in place.

In another embodiment disclosed in the above patent, a rigid needle implant containing radioactive segments, with break points, is inserted into the tumor. The needle implant is made of a bio-absorbable polymer that is rigid enough to be driven into the tumor without deflection and without the use of a separate hollow needle. When the proper depth is reached with the rigid polymer needle, the remaining, uninserted portion of the needle is broken off. This embodiment has the disadvantage of the above embodiment, in that being too rigid, the implant does not follow the tumor as it shrinks back to its normal size.

In U.S. Pat. No. 6,163,947, Coniglione, issued Dec. 26, 2000, and incorporated herein by reference, a string of hollow seeds described in U.S. Pat. No. 5,713,828, issued Feb. 3, 1998, also incorporated herein by reference, are strung onto a thin strand of suture material to form an array of seeds. This string of seeds is delivered into the tumor site placed within a hollow needle. Since the hollow lumen of the seeds are substantially smaller in diameter in relation to the outside diameter of the seed body, the string of suture material must be substantially smaller in diameter than the seeds themselves. The resulting diameter of the suture makes the suture axially weak and the suture can fold up between the seeds within the needle lumen as pressure is applied on the proximal end of the strand within the needle. Thus, the difference in diameter between the seed and the thin suture material makes the assembly susceptible to collapse from axial force applied on the proximal end, resulting in jamming of the assembly within the needle lumen and/or the assembly not maintaining the proper desired spacing between radioactive seeds as the assembly is expelled into the treatment site.

One relevant reference discloses modification of the needle structure to include a reloadable cartridge. In such reference the needle is inserted and as a cartridge of seeds is emptied, the plunger of the device is withdrawn and anew cartridge containing radioactive seeds is loaded into the syringe (Moore, U.S. Pat. No. 4,086,914, issued May 2, 1978). Another reference offers a device for implanting individual seeds in a planar dispensing device with multiple needles to ensure accurate placement of the seeds relative to one another and the treatment site (Kirsch, U.S. Pat. No. 4,167,179 issued September 1979). Another reference disclosed a shielding devices for bead strands which prevents radiation exposure for health care personnel performing treatment with the radioactive seeds (Windarski, U.S. Pat. No. 4,509,506 issued April 1985). All of the above references are incorporated herein by reference.

In another technique for treating tumors disclosed in U.S. Pat. No. 5,460,592 and incorporated herein by reference, seeds are held in a woven or braided bio-absorbable carrier such as a braided suture. The carrier with the seeds laced therein is then secured in place to form a suitable implant. This braided assembly exhibits many drawbacks, as and when the braided assembly is placed into the tumor. The needle that carries the braided assembly must be blocked at the distal end to prevent body fluids from entering the lumen. If body fluid reaches the braided assembly while the assembly is still in the lumen of the needle, the braided assembly can swell and jam in the lumen. Because the assembly is made of a braided tubular material, it is difficult to push the assembly out of the needle. As the needle is withdrawn from the tumor, pressure on the proximal end of the braided assembly causes the braid to expand and jam inside the lumen of the needle. Finally, if the braided strand is successfully expelled from the needle, the relative spacing of the seeds may not be maintained, if the braided material has collapsed.

Other references that address such implants and materials include the following, all of which are incorporated herein by reference.

U.S. Patent Documents:

U.S. Pat. No. 1,578,945 issued January 1923 to Withers.

U.S. Pat. No. 2,067,589 issued January 1937 to Antrim.

U.S. Pat. No. 3,351,049 issued November 1967 to Lawrence.

Medi-Physics brochure entitled "I-125 Seeds.RTM. In Carrier", Model No. 6720.

Medi-Physics brochure entitled "I-125 Seed.RTM. Source Model 6711".

Martinez et al., Int. J. Radiation Oncology Biol. Phys., vol. 5, No. 3, March 1979, pp. 411–413.

SUMMARY OF SOME OF THE ASPECTS OF THE INVENTION

Accordingly, the present invention cures and addresses the disadvantages exhibited in the prior art devices and implants. What is desired is to provide a bio-absorbable carrier material having seeds disposed within the material, with the seeds being accurately spaced a predetermined distance from one another, with the seeds repeatably maintaining that spacing, even after being introduced into the body.

It is further desired that an elongated member with seeds be sufficiently rigid axially to allow expulsion of the member from a needle while maintaining the spacing between seeds, and that the member be flexible and pliable enough to move with the tissue as the tissue shrinks back to pre-operative size.

Accordingly, some of the objectives of the present invention include providing an elongated member with seeds dispersed throughout, which obviates the aforementioned disadvantages and allows placement of the seeds in accurate positions to provide the desired interstitial radiation dose to the location derived from a preoperative dosimeter plan.

A further object of the present invention is to provide a delivery system for interstitial radiation therapy, which is faster and easier to use than prior art systems.

Another object of the present invention is a delivery system that causes a minimum of trauma to tissue.

Yet another object of the present invention is a delivery system that allows for control of the radiation dosage given the tissue. Still further objects of the present invention is a delivery system that can be used and placed with precision, and that maintains the position of the implant after the implantation, until the bio-compatible material dissolves and the seeds have become inert. In another aspect the bio-compatible material is selected to absorb about when the half-life of the radioactive seeds is reached.

A further aspect is to have the implant be echogenic.

In accordance with an embodiment of the invention, the delivery system comprises a substantially axially stiff and radially flexible elongated member that is bio-absorbable in living tissue. The member has a length that greatly exceeds its width or diameter. The elongated member has a plurality of radioactive seeds dispersed therein in a predetermined array.

In another embodiment, the substantially axially stiff and radially flexible elongated member comprises a single continuous monofilament element of bio-compatible material that has a plurality of seed sources molded thereon. The bio-compatible material can be preferably a bio-absorbable polymer or copolymer material that encapsulates the plurality of radioactive seeds.

A further embodiment of the invention is characterized as a substantially constant diameter solid elongated matrix member of a bio-absorbable polymer with seeds positioned therein at predetermined spacing along its length, whose diameter is a close fit to the needle lumen, thus preventing collapse as axial force is applied on the proximal end of the elongated matrix member. The space between the seed sources is maintained throughout the insertion and expulsion of the elongated matrix member. The diameter of the polymer between the seeds maybe slightly reduced in relation to the overall diameter of the elongated matrix member, but is of sufficient diameter so as to not allow collapse of the matrix member within the needle lumen.

The present embodiment of the invention further allows for variation in any spacing between seeds, as the semi-rigid, deflecting elongate member could be produced under a doctor's prescription for each patient, with optimal seed distribution for a particular patient's treatment program.

Thus one object of the invention is to provide an implant that can be custom made as specified by a prescription for an individual patient.

The present embodiment of the invention allows for a therapeutic element comprising hollow radioactive seeds positioned on a suture strand composed of material that as an assembly is axially rigid and radially flexible. The material may be composed of a bioabsorbable polymer. Additionally, heating of the polymer may cause it to swell, thereby locking the seeds in position on the strand.

Further aspects, objects, advantage and embodiment of the invention can be understood from the specification, the figures and the claims.

DETAILED DESCRIPTION OF THE PREFERRED EMBODIMENT

Figure 1:
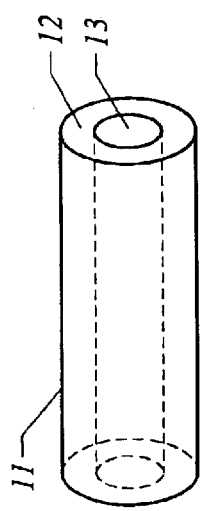
FIG. 1 is an enlarged side view of a tubular shaped, hollow radioactive seed element with a central bore.

Unlike prior brachytherapy devices, the present invention utilizes a polymer-based suture inserted through the bore of a tubular shaped seed. This device provides for improved brachytherapy because radioactive seeds can be conveniently threaded onto suture material that is readily available in any treatment setting. Suture material, rigid rods or other biocompatible connecting members can be passed through the center of the device and then the position of the seed elements can be fixed as needed for treatment. Heating the polymer strands with the seeds in position will cause the polymer to expand and fix the seeds in position. The polymer can be bioabsorbable. Examples of polymers are shown in Table 1. The hollow tube design of the device permits tissue to grow into the hollow space, particularly after the polymer suture material has been absorbed, further minimizing migration of the seed. The tube shaped substrate can be made of a material that is essentially transparent to radiation, such as titanium. In addition to the radioisotopes listed in Table 1, the seed can be coated with a isotope that will convert to radioactive emissions. The precursor isotope can be activated to varying degrees which would allow customization of the emission given off by a single seed because the amount of irradiation and subsequent activation can be varied for different treatment strategies. The hollow tube-shaped substrate can be formed from a material transparent to radiation emitted by the therapeutic isotope. Covering the radioactive layer with a sealing layer prevents direct contact between the radioactive isotope and health care workers, or its escape into the surrounding environment or tissues.

In accordance with an embodiment of the invention, a substantially axially, semi-rigid and radially or laterally flexible elongated member made of material, which is bio-absorbable in living tissue, is provided for insertion in tumors. A plurality of radioactive seeds are encapsulated and positioned in a predetermined array in the member in the desired spaced relationships.

The seeds can be of various types having low energy and low half-life such as Iodine seeds, known as I-125 seeds, consisting of a welded titanium capsule containing iodine 125 absorbed on a silver rod, or Palladium 103 seeds. Examples of radioactive seeds used to manufacture the therapeutic element appear in Table 1 below.

TABLE 1

Seed Manufacturers and Common Types of Seeds.

| PART NUMBER | MANUFACTURER | SEED NAME |
| --- | --- | --- |
| | IODINE$^{125}$ | |
| 80040-A | Amersham 6702 | OncoSeed |
| 80040-B | Amersham 6711 | RAPID Strand |
| 80040-C | North American Scientific | IoGold |
| 80040-D | Best Industries | BEST Iodine-125 |
| 80040-E | Bebig | Symmetra |
| 80040-F | Mills Biopharmaceuticals | ProstaSeed |
| 80040-G | Syncor | PharmaSeed |
| 80040-H | International Isotopes | IsoStar |
| 80040-I | Implant Sciences | I-Plant |
| 80040-J | International Brachytherapy | InterSource-125 |
| 80040-K | Source Tech | STM1251 |
| 80040-L | DRAXIMAGE, Inc. | BrachySeed |
| | PALLADIUM$^{103}$ | |
| 80035-A | North American Scientific | Pd Gold |
| 80035-B | Theragenics | Theraseed 200 |
| 80035-C | Best Industries | BEST Palladium-103 |
| 80035-D | International Brachytherapy | InterSource 103 |

Additionally, seeds can be manufactured using iridium 192, cesium 131, gold 198, yttrium 90 and phosphorus 32. Further radioactive isotopes used to manufacture seeds are not limited to these examples, but can include other sources of different types of radiation. In addition it is to be understood that other types of seeds can be used. In particular, seeds such as those described in U.S. Pat. No. 6,248,057, which patent is incorporated herein by reference and which is entitled Absorbable Brachytherapy and Chemotherapy Delivery Devices and Methods, can be used with the present invention. These seeds include radiation delivery devices, drug delivery devices, and combinations of radiation and drug delivery devices in the form of beads, seeds, particles, rods, gels, and the like. These particular seeds are absorbable. In such seeds, the bio-absorbable structure can have a predefined persistence which is substantially longer than a half-life of the radioactive element contained in the bio-absorbable structure. These above bio-absorbable seeds can be used in the same manner as the seeds described herein with respect to the invention.

The substantially axially, semi-rigid, and radially or laterally flexible elongated member maybe made of any of the natural and/or synthetic bio-compatible and bio-absorbable materials. Natural and synthetic polymers and copolymers can be used. Examples of synthetic bio-absorbable polymer materials are the polymers and copolymers of glycolide and lactide, polydioxanone and the like. Such polymeric materials are more fully described in U.S. Pat. Nos. 3,565,869, 3,636,956, 4,052,988 and European Patent Application 30822 all of which are incorporated herein by reference. Specific examples of bio-absorbable polymeric materials that can be used to produce the substantially axially stiff and radially flexible elongated member of embodiment of the present invention are polymers made by ETHICON, Inc., Somerville, N.J., under the trademarks "MONOCRYL" and "MAXON" which material is incorporated herein by reference.

Table 2 below provides examples of polymers (and manufacturers) suitable for use in producing embodiments of the therapeutic member of the invention. A further discussion of such biodegradable polymers can be found in an article by John C. Middleton and Arthur J. Tipton entitled "Synthetic Biodegradable Polymers as Medical Devices," published March 1998 in Medical Plastics and Bio-materials which article is incorporated herein by reference.

TABLE 2

Biodegradable polymers, properties and degradation time.

| POLYMER | MELTING POINT (° C.) | GLASS-TRANSITION TEMP (° C.) | MODULUS (Gpa)[a] | DEGRADATION TIME (MONTHS)[b] |
|---|---|---|---|---|
| PGA | 225–230 | 35–40 | 7.0 | 6 to 12 |
| LPLA | 173–178 | 60–65 | 2.7 | >24 |
| DLPLA | Amorphous | 55–60 | 1.9 | 12 to 16 |
| PCL | 58–63 | (−65)–(−60) | 0.4 | >24 |
| PDO | N/A | (−10)–0 | 1.5 | 6 to 12 |
| PGA-TMC | N/A | N/A | 2.4 | 6 to 12 |
| 85/15 DLPLG | Amorphous | 50–55 | 2.0 | 5 to 6 |
| 75/25 DLPLG | Amorphous | 50–55 | 2.0 | 4 to 5 |
| 65/35 DLPLG | Amorphous | 45–50 | 2.0 | 3 to 4 |
| 50/50 DLPLG | Amorphous | 45–50 | 2.0 | 1 to 2 |

[a]Tensile or flexural modulus.
[b]Time to complete mass loss. Rate also depends on part geometry.

The final hardness of the polymer of elongate member should preferably be in a range from 20 to 80 durometer and more preferably in the range of 20–40 durometer. The bio-absorbable material should preferably be absorbed in living tissue in a period of time of from about 70 to about 120 days, but can be manufactured to be absorbed anywhere in a range from 1 week to 1 year, depending on the therapeutic plan for each specific patient. Preferably the bio-absorbable material is selected to absorb about when the half-life of the radioactive seeds is reached.

In FIG. 1, the tubular shaped, hollow radioactive seed 11 is pictured. The seed 11 has ends 12 and a bore 13 which passes through the center of the seed 11 and communicates with the ends 12 of the seed 11.

Figure 2:
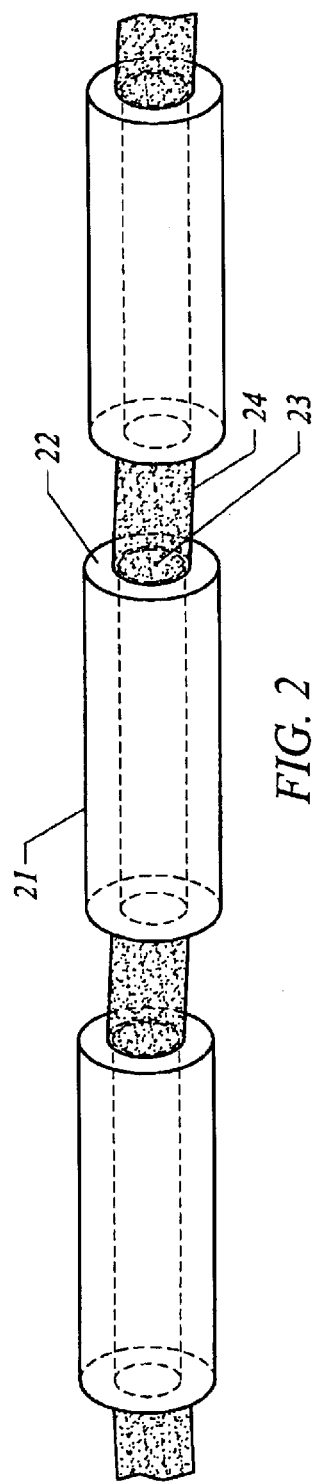
FIG. 2 is an enlarged side view of an embodiment of the invention showing several tubular shaped, hollow radioactive seeds with polymer through the seed bore to form a therapeutic element.

FIG. 2 shows a side view of a section of the therapeutic element. The tubular shaped radioactive seed 21 as described in FIG. 1 is shown. Similar to FIG. 1, the seed 21 has ends 22, and the hollow bore 23 through the center of the seed 21 communicates with the ends 22 of the seed 23. Also shown is the material 24 that passes through the bore 23 of the seed 21 and makes the assembly axially rigid and radially or laterally flexible. The material 24 maybe a polymer as described above in Table 2. The material 24 may be inserted into the bore 23 of the seed 21 as a suture and then heated, causing the suture to expand and fix the seeds 21 in position. More particularly, the suture material is fashioned by molding from a material 24 that is axially rigid, yet radially flexible. Then the suture is inserted into the central bore of the tubular shaped radioactive seed elements. The seed elements 21 are placed along the suture with predetermined spacing that is specific to the desired treatment. The suture or the entire therapeutic element can then be heated, causing the material 24 to expand and fix the seeds 21 in place, while expanding between the seeds 21 to a width that is greater than the bore 23 of the hollow seeds 21. Alternatively, the seeds 21 can be fixed in place by crimping the suture at either end of the hollow seed 21 into a shape that does not fit through the seed bore. Such crimping can fix the seeds in place. Once crimping has occurred, if desired and applicable according to the type of suture used, the strand can be heated in order to cause the suture to expand and further fix the seeds in place. Using such a crimping technique, the spacing between each seed pair can be independently set in accordance to a treatment plan as set forth below.

Alternatively, the seeds 21 maybe placed in a mold and the material 24 flowed into cavities between the seeds 21 and into the hollow bore 23 of the seed. Upon cooling, the material 24 can expand and fix the seeds 21 into position along the therapeutic element. More particularly, the seeds 21 may be placed in a mold that fits the seeds 21 and a cavity that extends between the seeds 21. The synthetic polymer 24 is introduced into the mold at a temperature that is above the melt point of the polymer 24. The polymer 24 flows into the bore 23 of the seeds 21 and fills in the spaces between the seeds 21. After the mold has cooled, it is disassembled, and the finished elongated member is removed. Because the polymer 24 flows at temperatures significantly greater than 250° F., the therapeutic element can easily be steam sterilized before implantation.

Figure 3:
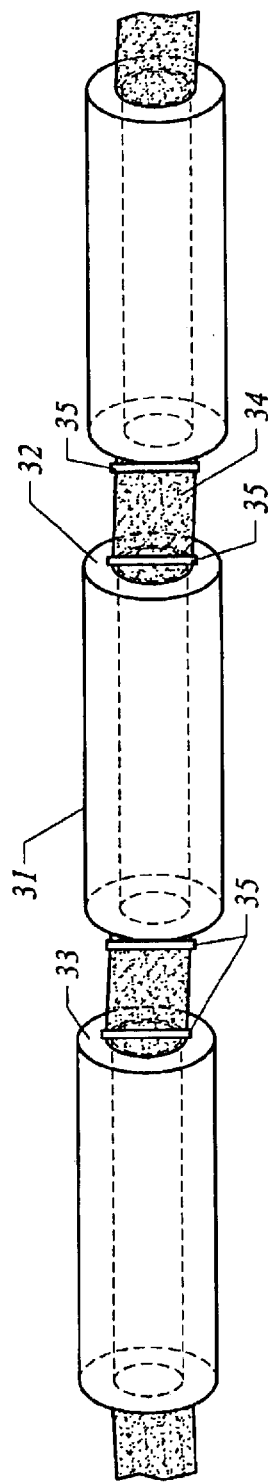
FIG. 3 is an enlarged side view of yet another embodiment of the invention.

FIG. 3 illustrates another embodiment of the present invention. The seeds 31 can be spaced according to a received prescription plan for a given patient. The seeds 31 can then be fixed into position by crimping 35 the suture material or polymer 34 that borders the seed, or crimping the suture material bordering the seed 31 and heating the suture material. The crimped sections 35 do not fit inside the hollow bore 33 of the seeds 31. Thus, the seeds 31 are fixed into position by the crimped sections 35 of suture or polymer 34 that occur at the edge of the seeds, near the end 32 of the seed.

The manufacturing process also can make the member echogenic. In the case of the molding of the elongated member, air can be entrapped in the polymer material. During the cooling stage of the molding process, the mold is placed in a vacuum chamber and the air in the chamber is evacuated. This causes the entrapped air in the mold to come out of solution from the polymer, and as the mold cools, this air is entrapped within the cooling polymer in the form of or minute bubbles suspended in the plastic.

Air is a strong reflector of ultrasound energy, since the inherent impedance of air is many times greater than body tissue. When the elongated member is introduced into the body and imaged with ultrasound, the elongated member is clearly visible in the resulting image, and is thus echogenic.

The resulting elongated member is now a single solid monofilament of the polymer with the seeds spaced along the monofilament and encapsulated at the appropriate intervals. The member is generally very radially flexible such that it can be bent back upon itself in a circle without kinking. However, the member is axially rigid and has sufficient column strength along its longitudinal axis so that the member can be urged out of a hollow needle without the member folding upon itself. Again, the intervals can be selected to be any distance or combination of distances that are optimal for the treatment plan of the patient.

Based on the above it is evident that the present invention provides for an embodiment having a biodegradable polymer inserted through the bore of tubular-shaped hollow seeds. The seeds can be spaced in custom manner so that each member or strand is designed for the particular patient. That is to say that the spacing between each seed pair in a strand or member can be different for each seed pair. Further each individual strand can have an entirely different seed spacing pattern than the next strand or member. Characteristically or typically for a surgical procedure, up to twenty-five of such strands or members are used to encircle the organ or tumor that is affected.

In other embodiments, the strand or member can be made with the incorporation of drugs and/or hormones and/or other therapeutics which are embedded in or formed in the polymer and/or seeds. Thus the embodiment of the invention can deliver not only radioactive seeds, but such therapeutic drugs, hormones and other therapeutic devices. In addition the strand or member can deliver heated seeds such as provided by ATI Medical. Then seeds can be preferably heated to from about six (6) degrees centigrade to about seventy (70) degrees centigrade prior to being inserted into a patient in a preferred embodiment. ATI Medical is located at (www.ATImedical.com), and reference to such heated seeds is incorporated herein by reference.

It should be understood that other seed types can be used with the present invention. Thus for example in addition to the above encapsulated seeds, seeds which are made of radioactive or coiled wires can be embedded in the polymer and be within the spirit and scope of the invention. These seeds can be individual seeds which are spaced within a polymer or a continuous seed which extends the length of the strand or member.

Further to the invention, as discussed above, it should be understood that the strand or member can be made echogenic by the incorporation of, for example, air bubbles in the polymer spaces between the seeds. These air bubbles or pockets can be formed in the polymer in ways identified above and other ways known to one of skill in the art.

According to the above, the advantages of the improved delivery system submitted of the present invention are:

1. The substantially axially stiff and radially flexible elongated member allows controlled placement of the plurality of radioactive seeds that are encapsulated and positioned in a predetermined array along the member without migration of the individual radioactive seeds during the time the seeds are treating the tumor.

2. The fixed linear positioning of the seeds minimizes "hot" and "cold" radiation spots due to undesirable movement of the seeds.

3. The axial stiffness of the elongated member allows the elongated member to be urged out of the needle as the needle is withdrawn, without the member jamming in the needle, by collapsing or expanding as the needle is withdrawn from the tumor site.

4. The radial flexibility of the elongated member allows locational accuracy to be maintained as the gland shrinks to pre-procedural size, as the swelling that occurs during tissue disruption and needle manipulation recedes.

5. Increased speed of implant resulting in reduced surgical time and health care provider radiation exposure.

Method of Delivering Customized Strands and/or Members Per a Therapeutic Prescription As is known in the industry, there is software which can be used to provide branchytherapy treatment planning guides which are customized for each individual patent. Such software is provided by Rossmed which is located at Ross Medical, 7100 Columbia Gateway Drive, Suite 160, Columbia, Md. 21046. This particular software, which is incorporated herein by reference, is known as the Strata suite, which software helps physicians to develop and visualize low dose rate brachytherapy treatment plans for treating malignant tumors in human tissue. The treatments entail the use of radioactive seed sources which are implanted adjacent to the malignant tissue. The Strata software uses imaging to create a three dimensional reconstruction of the patient's anatomy. The software is able to plan the placement of the seeds within the target. The radiation dose that is delivered to the target can be computerized and visualized using the software. The software can then specify an optimal number of strands or members along with optimal seed dosages and spaces between seeds. At times the loading plans so specified cannot be optimized by the physician in preparing the seed and spacer loads for the needles, as the spacers come in only predefined lengths.

Accordingly with the present invention, the software can be used to prepare a prescription which optimizes the number of members or strands, and placement and spacing of seeds for each of the strands or members. This optimization plan can then be sent to a manufacturing site. By using the techniques of an embodiment of the present invention, an optimized strand or member can be created with the specified number of seeds and the specified distances between each seed pair. Once this prescription is filled at the manufacturing site, the custom strand or member can be sent back to the physician for treatment of the patient. With such an arrangement, radiation patterns can be optimally established for the treatment of each patient. Further the preparation time for the physician is greatly diminished as the physician does not have to hand assemble and hand load the seeds and spacers into the needle.

Further even if the physician were to use a prescription provided by the above software, with prior manufacturing techniques, the physician would only receive from the manufacturing facility a strand or member which has seeds spaced at predefined intervals, which are the lengths or the pre-manufactured spacers. Accordingly optimal treatment as provided by the custom strands or members manufactured according to the present invention could not be realized.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A therapeutic element comprising:
   radioactive seed elements;
   said radioactive seed elements being tubular in shape with a bore;
   an elongate member being expandable upon heating;
   said elongated member being inserted inside said bore of said radioactive seed elements and fixed by heating to said seed elements in order to cause the seed elements to be captured at intervals.

2. The therapeutic element set forth in claim 1 wherein said elongate member in combination with the seed elements is axially rigid and radially flexible.

3. The therapeutic element set forth in claim 1 wherein said elongate member in combination with the seed elements is sufficiently axially rigid to prevent jamming or collapsing while being pushed out of a needle.

4. The therapeutic element set forth in claim 1 wherein said elongate member is impregnated with a hormone.

5. The therapeutic element set forth in claim 1 wherein said elongate member is impregnated with a drug.

6. The therapeutic element set forth in claim 1 wherein said radioactive seed elements are positioned at various intervals along the length of said elongate member.

7. The therapeutic element set forth in claim 1 wherein said radioactive seed elements contain a hormone.

8. The therapeutic element set forth in claim 1 wherein said radioactive seed elements contain a drug.

9. The therapeutic element set forth in claim 1 wherein the elongate member is comprised of a material that is bioabsorbable in a time that is about a half-life of said radioactive seeds.

10. The therapeutic element set forth in claim 1 wherein said radioactive seed elements contain an isotope consisting of the group iodine 125, palladium 103, iridium 192, cesium 131, gold 198 yttrium 90 and phosphorus 32.

11. The therapeutic element set forth in claim 1 wherein said elongate member is composed of a bio-absorbable material.

12. The therapeutic element set forth in claim 1 wherein said elongate member is composed of a bio-absorbable material absorbed by living tissue within about 70 to 120 days.

13. The therapeutic element set forth in claim 1 wherein the elongate member is comprised of a bio-absorbable material is selected from the group consisting polymers and copolymers of glycolide, lactide and polydiaxanone.

14. The therapeutic element set forth in claim 1 wherein the elongate member has a durometer of 20 to 40.

15. The therapeutic element set for in claim 1 wherein the elongate member has a durometer of 20 to 80.

16. The therapeutic element set forth in claim 1 wherein said elongate member is echogenic.

17. The therapeutic element set forth in claim 1 wherein said elongate member has air bubbles.

18. The therapeutic element set forth in claim 1 wherein said elongate member is laterally flexible.

19. The therapeutic element set forth in claim 1 wherein said radioactive seed element is encapsulated.

20. A therapeutic element comprising:
    radioactive seed elements that are tubular in shape with a bore;
    an elongated member comprised of a polymer being expandable upon heating;
    said elongated member being inserted inside said bore of said radioactive seed elements and fixed by heating to said seed elements in order to cause the seed elements to be captured at intervals.

21. The therapeutic element set forth in claim 20 wherein said polymer is impregnated with a hormone.

22. The therapeutic element set forth in claim 20 wherein said polymer is impregnated with a drug.

23. The therapeutic element set forth in claim 20 wherein said radioactive seed elements are positioned at various intervals along the length of said elongate member.

24. The therapeutic element set forth in claim 20 wherein said seed elements radioactive contain a hormone.

25. The therapeutic element set forth in claim 20 wherein said radioactive seed elements contain a drug.

26. The therapeutic element set forth in claim 20 wherein the polymer is bioabsorbable in a time that is about a half-life of said radioactive seeds.

27. The therapeutic element set forth in claim 20 wherein said radioactive seeds contain an isotope consisting of the group iodine 125, palladium 103, iridium 192, cesium 131, gold 198 yttrium 90 and phosphorus 32.

28. The therapeutic element set forth in claim 20 wherein said polymer bio-absorbable.

29. The therapeutic element set forth in claim 20 wherein said polymer is a bio-absorbable in living tissue within about 70 to 120 days.

30. The therapeutic element set forth in claim 20 wherein the polymer is selected from the group consisting of polymers and copolymers of glycolide, lactide and polydiaxanone.

31. The therapeutic element set forth in claim 20 wherein the polymer has a durometer of 20 to 40.

32. The therapeutic element set for in claim 20 wherein the polymer has a durometer of 20 to 80.

33. The therapeutic element set forth in claim 20 wherein said polymer is echogenic.

34. The therapeutic element set forth in claim 1 wherein said polymer has air bubbles.

35. The therapeutic element set forth in claim 20 wherein said elongate member is laterally flexible.

36. The therapeutic element set forth in claim 20 wherein the polymer has a durometer of 20 to 40.

37. The therapeutic element set for in claim 20 wherein the polymer has a durometer of 20 to 80.

38. A therapeutic element comprising:
    radioactive seed elements;
    said radioactive seed elements being tubular in shape;
    an elongated solid member being expandable upon heating;
    said elongated solid member being inserted inside said radioactive seed elements;
    and said radioactive seed elements dispersed along said elongated solid member, and said elongated solid member is fixed by heating to said seed elements in order to cause the seed elements to be captured at intervals, wherein the seed elements and the member so assembled are axially rigid and radially flexible.

39. A therapeutic element comprising:

radioactive seed elements;

said radioactive seed elements being tubular in shape with a bore;

an elongated member;

said elongated member being inserted inside said bore of said radioactive seed elements and fixed by crimping to said seed elements in order to cause the seed elements to be captured at intervals, where at least some of the intervals can be independently set to a desired length.

40. The therapeutic element set forth in claim 39 wherein said elongate member in combination with the seed elements is axially rigid and radially flexible.

41. The therapeutic element set forth in claim 39 wherein said elongate member is impregnated with a hormone.

42. The therapeutic element set forth in claim 39 wherein said elongate member is impregnated with a drug.

43. The therapeutic element set forth in claim 39 wherein said radioactive seed elements are positioned at various intervals along the length of said elongate member.

44. The therapeutic element set forth in claim 39 wherein said radioactive seed elements contain a hormone.

45. The therapeutic element set forth in claim 39 wherein said radioactive seed elements contain a drug.

46. The therapeutic element set forth in claim 39 wherein the elongate member is comprised of a material that is bioabsorbable in a time that is about a half-life of said radioactive seeds.

47. The therapeutic element set forth in claim 39 wherein said radioactive seed elements contain an isotope consisting of the group iodine 125, palladium 103, iridium 192, cesium 131, gold 198 yttrium 90 and phosphorus 32.

48. The therapeutic element set forth in claim 39 wherein said elongate member is composed of a bio-absorbable material.

49. The therapeutic element set forth in claim 39 wherein said elongate member is composed of a bio-absorbable material absorbed by living tissue within about 70 to 120 days.

50. The therapeutic element set forth in claim 39 wherein the elongate member is comprised of a bio-absorbable material is selected from the group consisting of polymers and copolymers of glycolide, lactide and polydiaxanone.

51. The therapeutic element set forth in claim 39 wherein the elongate member has a durometer of 20 to 40.

52. The therapeutic element set for in claim 39 wherein the elongate member has a durometer of 20 to 80.

53. The therapeutic element set forth in claim 39 wherein said elongate member is echogenic.

54. The therapeutic element set forth in claim 39 wherein said elongate member has air bubbles.

55. The therapeutic element set forth in claim 39 wherein said elongate member is laterally flexible.

56. The therapeutic element set forth in claim 39 wherein said seed element radioactive is encapsulated.

57. A therapeutic element comprising:

radioactive seed elements that are tubular in shape with a bore;

an elongated member comprised of a polymer;

said elongated member being inserted inside said bore of said tubular radioactive seed elements and fixed by crimping to said seed elements in order to cause the seed elements to be captured at intervals, where at least some of the intervals can be independently set to a desired length.

58. The therapeutic element set forth in claim 57 wherein said polymer is impregnated with a hormone.

59. The therapeutic element set forth in claim 57 wherein said polymer is impregnated with a drug.

60. The therapeutic element set forth in claim 57 wherein said radioactive seed elements are positioned at various intervals along the length of said elongate member.

61. The therapeutic element set forth in claim 57 wherein said radioactive seed elements contain a hormone.

62. The therapeutic element set forth in claim 57 wherein said radioactive seed elements contain a drug.

63. The therapeutic element set forth in claim 57 wherein the polymer is bioabsorbable in a time that is about a half-life of said radioactive seeds.

64. The therapeutic element set forth in claim 57 wherein said tad radioactive seeds contain an isotope consisting of the group iodine 125, palladium 103, iridium 192, cesium 131, gold 198 yttrium 90 and phosphorus 32.

65. The therapeutic element set forth in claim 57 wherein said polymer bio-absorbable.

66. The therapeutic element set forth in claim 57 wherein said polymer is a bio-absorbable in living tissue within about 70 to 120 days.

67. The therapeutic element set forth in claim 57 wherein the polymer is selected from the group consisting of polymers and copolymers of glycolide, lactide and polydiaxanone.

68. The therapeutic element set forth in claim 57 said polymer is echogenic.

69. The therapeutic element set forth in claim 57 wherein said polymer has air bubbles.

70. The therapeutic element set forth in claim 57 wherein said elongate member is laterally flexible.

71. A therapeutic element comprising:

radioactive seed elements;

said radioactive seed elements being tubular in shape;

an elongated solid member;

said elongated solid member being inserted inside said radioactive seed elements;

and said radioactive seed elements dispersed along said elongated solid member, and said elongated solid member is fixed by crimping to said seed elements in order to cause the seed elements to be captured at intervals, wherein the seed elements and said elongated solid member so assembled are axially rigid and radially flexible, and wherein at least some of the intervals can be independently set to a desired length.

72. A therapeutic element comprising:

an elongated member made of a polymeric material;

a plurality of radioactive seed elements, wherein each of said radioactive seed elements is tubular in shape and has a hollow bore;

said elongated member being axially rigid and radially flexible; and said plurality of radioactive seed elements being affixed to said elongated member; said elongated member passing through each said hollow bore of each seed.

73. The therapeutic element of claim 72, wherein said elongated member is formed by flowing heated polymeric material through the hollow bores of said plurality of seeds, and allowing said heated polymeric material to cool.

* * * * *

UNITED STATES PATENT AND TRADEMARK OFFICE
CERTIFICATE OF CORRECTION

PATENT NO. : 6,786,858 B2
DATED : September 7, 2004
INVENTOR(S) : Richard A. Terwilliger It is certified that error appears in the above-identified patent and that said Letters Patent is hereby corrected as shown below:

Column 11,
Line 60, change "for" to -- forth --

Column 12,
Line 20, change "said seed elements radioactive contain a hormone." to
-- said radioactive seed elements contain a hormone. --
Line 46, change "1" to -- 20 --

Column 13,
Line 47, change "for" to -- fourth --
Line 55, change "said seed element radioactive is encapsulated." to -- said radioactive seed element is encapsulated. --

Column 14,
Line 28, change "57, said" to -- 57, wherein said --

Signed and Sealed this

Twenty-second Day of February, 2005

JON W. DUDAS
*Director of the United States Patent and Trademark Office*